US012799523B2

(12) United States Patent
Ghadiri et al.

(10) Patent No.: US 12,799,523 B2
(45) Date of Patent: Nov. 17, 2026

(54) NUCLEOTIDE REAGENT SOLUTIONS

(71) Applicant: LIFE TECHNOLOGIES CORPORATION, Carlsbad, CA (US)

(72) Inventors: Jamsheed Ghadiri, Santa Clara, CA (US); Karta Atehortua-Khalsa, Castro Valley, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 391 days.

(21) Appl. No.: 18/545,099

(22) Filed: Dec. 19, 2023

(65) Prior Publication Data

US 2024/0117412 A1 Apr. 11, 2024

Related U.S. Application Data

(63) Continuation of application No. 17/571,360, filed on Jan. 7, 2022, now Pat. No. 11,873,526, which is a continuation of application No. 16/654,629, filed on Oct. 16, 2019, now Pat. No. 11,230,730.

(60) Provisional application No. 62/746,542, filed on Oct. 16, 2018.

(51) Int. Cl.
*C12Q 1/68* (2018.01)
*C12Q 1/6806* (2018.01)

(52) U.S. Cl.
CPC .................................. *C12Q 1/6806* (2013.01)

(58) Field of Classification Search
CPC .................................................... C12Q 1/6869
See application file for complete search history.

(56) References Cited

U.S. PATENT DOCUMENTS

| | | | |
|---|---|---|---|
| 7,993,839 | B2 | 8/2011 | Nelson et al. |
| 9,035,035 | B2 | 5/2015 | Cherkasov et al. |
| 2008/0103058 | A1 | 5/2008 | Siddiqi |
| 2009/0130720 | A1 | 5/2009 | Nelson et al. |
| 2009/0155859 | A1 | 6/2009 | Nelson et al. |
| 2010/0028862 | A1 | 2/2010 | Jarvis et al. |
| 2010/0029494 | A1 | 2/2010 | Cherkasov et al. |
| 2014/0093878 | A1 | 4/2014 | Nelson et al. |
| 2017/0211134 | A1 | 7/2017 | Marma et al. |
| 2017/0298415 | A1 | 10/2017 | Heller et al. |
| 2018/0135108 | A1 | 5/2018 | Etchebarne |
| 2018/0235206 | A1 | 8/2018 | Laughlin et al. |

OTHER PUBLICATIONS

PCT/US2019/056514, Partial Search Report, Jan. 24, 2020.
PCT/US2019/056514, Search Report and Written Opinion, Mar. 12, 2020.

*Primary Examiner* — Kenneth R Horlick

(57) ABSTRACT

A reagent solution includes water, a nucleotide, and tris(2-carboxyethyl)phosphine in a range of 0.5 μM to 1000 μM. The reagent solution can further include a non-ionic surfactant in an amount of 0.001% to 1% or a biocidal agent in an amount of 0.001% to 1%. The reagent solution can include salts, such as sodium chloride or magnesium sulfate.

19 Claims, 3 Drawing Sheets

NUCLEOTIDE REAGENT SOLUTIONS

CROSS-REFERENCE TO RELATED APPLICATION(S)

This application is a continuation of U.S. patent application Ser. No. 17/571,360, filed Jan. 7, 2022 (now U.S. Pat. No. 11,873,526), which is a continuation of U.S. patent application Ser. No. 16/654,629, filed Oct. 16, 2019 (now U.S. Pat. No. 11,230,730), which claims benefit of U.S. Provisional Application No. 62/746,542, filed Oct. 16, 2018, each of which is incorporated herein by reference in its entirety.

BACKGROUND

Increasingly, biological and medical research is turning to sequencing for enhancing biological studies and medicine. For example, biologist and zoologist are turning to sequencing to study the migration of animals, the evolution of species, and the origins of traits. The medical community is turned sequencing for studying the origins of disease, sensitivity to medicines, and the origins of infection. But, sequencing has historically been an expensive process, thus limiting its practice.

In particular, solutions including nucleotides are sensitive to temperature and pH changes. Many sequencing systems utilize reagent cartridges that are stored cold and replaced each run. Such single use reagent cartridges limit the exposure of reagents to room temperature and the diffusion of gases that can change pH. But, utilizing single use reagent cartridges is expensive and time consuming.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DESCRIPTION OF THE PREFERRED EMBODIMENT(S)

In an exemplary embodiment, a reagent solution includes a biomer and tris(2-carboxyethyl)phosphine (TCEP). In an example, a biomer is a nucleotide, a ribonucleotide, an amino acid, or a combination thereof. For example, the reagent solution can be an aqueous solution that includes water, a nucleotide, and TCEP. In addition, the reagent solution can include a surfactant, such as a non-ionic surfactant, or can include salts, such as sodium chloride or magnesium sulfate. Further, the reagent solution can include a biocidal agent, such as isothiazolinone or derivatives thereof. Such a reagent solution has been shown to have stability at room temperature and can be used as a bulk solution.

Embodiments of the reagent solution find use in sequencing processes and sequencing systems. Example sequencing systems can detect sequences based on the interaction of a nucleotide with a target sequence. In an example, the sequencing system can detect sequences using a sequencing-by-synthesis process. Examples of such a system include optical sequencing and pH-based sequencing. Other methods for detecting nucleic acid sequences include quantitative PCR. Embodiments of the reagent solution can also be useful in synthesizing nucleic acids, ribonucleic acids, or proteins.

Figure 1:
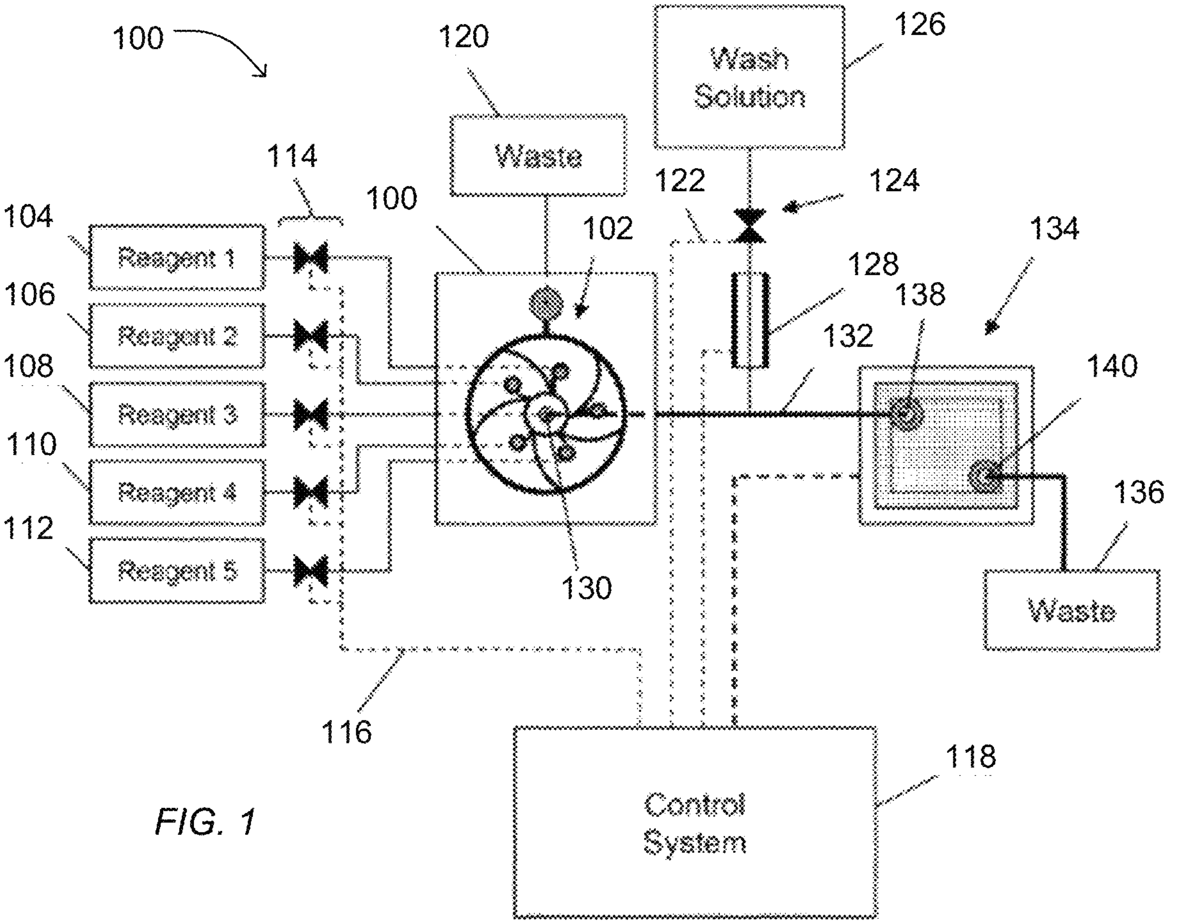
FIG. 1 includes an illustration of an example sequencing system.

FIG. 1 diagrammatically illustrates a system for carrying out pH-based nucleic acid sequencing. Each electronic sensor of the apparatus generates an output signal that depends on the value of a reference voltage. The fluid circuit permits multiple reagents to be delivered to the reaction chambers.

In FIG. 1, system 100 containing fluidics circuit 102 is connected by inlets to at least two reagent reservoirs (104, 106, 108, 110, or 112), to waste reservoir 120, and to biosensor 134 by fluid pathway 132 that connects fluidics node 130 to inlet 138 of biosensor 134 for fluidic communication. Reagents from reservoirs (104, 106, 108, 110, or 112) can be driven to fluidic circuit 102 by a variety of methods including pressure, pumps, such as syringe pumps, gravity feed, and the like, and are selected by control of valves 114. Reagents from the fluidics circuit 102 can be driven through the valves 114 receiving signals from control system 118 to waste container 120. Reagents from the fluidics circuit 102 can also be driven through the biosensor 134 to the waste container 136. The control system 118 includes controllers for valves, which generate signals for opening and closing via electrical connection 116.

The control system 118 also includes controllers for other components of the system, such as wash solution valve 124 connected thereto by electrical connection 122, and reference electrode 128. Control system 118 can also include control and data acquisition functions for biosensor 134. In one mode of operation, fluidic circuit 102 delivers a sequence of selected reagents 1, 2, 3, 4, or 5 to biosensor 134 under programmed control of control system 118, such that in between selected reagent flows, fluidics circuit 102 is primed and washed, and biosensor 134 is washed. Fluids entering biosensor 134 exit through outlet 140 and are deposited in waste container 136 via control of pinch valve regulator 144. The valve 144 is in fluidic communication with the sensor fluid output 140 of the biosensor 134.

Figure 2:
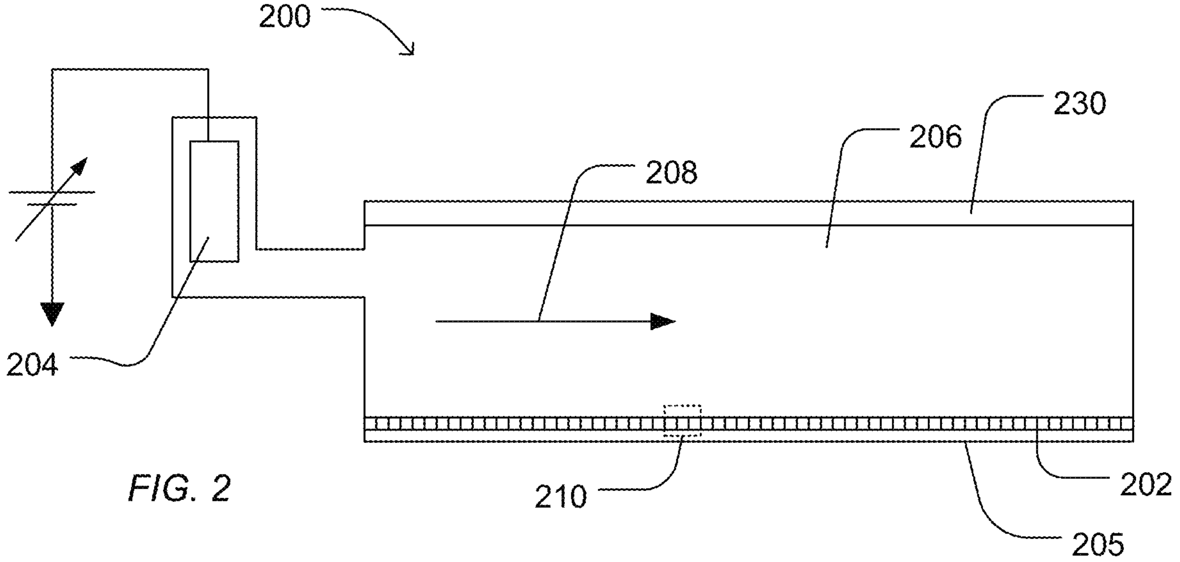
FIG. 2 includes an illustration of an exemplary system including a sensor array.

The device including the dielectric layer defining the well formed from the first access and second access and exposing a sensor pad finds particular use in detecting chemical reactions and byproducts, such as detecting the release of hydrogen ions in response to nucleotide incorporation, useful in genetic sequencing, among other applications. In a particular embodiment, a sequencing system includes a flow cell in which a sensory array is disposed, includes communication circuitry in electronic communication with the sensory array, and includes containers and fluid controls in fluidic communication with the flow cell. In an example, FIG. 2 illustrates an expanded and cross-sectional view of a flow cell 200 and illustrates a portion of a flow chamber 206. A reagent flow 208 flows across a surface of a well array 202, in which the reagent flow 208 flows over the open ends of wells of the well array 202. The well array 202 and a sensor array 205 together may form an integrated unit forming a lower wall (or floor) of flow cell 200. A reference electrode 204 may be fluidly coupled to flow chamber 206. Further, a flow cell cover 230 encapsulates flow chamber 206 to contain reagent flow 208 within a confined region.

Figure 3:
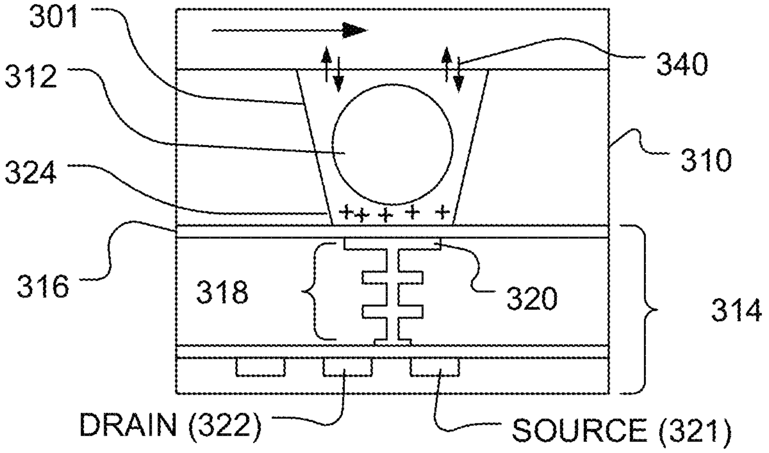
FIG. 3 includes an illustration of an exemplary sensor and associated well.

FIG. 3 illustrates an expanded view of a well 301 and a sensor 314, as illustrated at 210 of FIG. 2. The volume, shape, aspect ratio (such as base width-to-well depth ratio), and other dimensional characteristics of the wells may be selected based on the nature of the reaction taking place, as well as the reagents, byproducts, or labeling techniques (if any) that are employed. The sensor 314 can be a chemical field-effect transistor (chemFET), more specifically an ion-sensitive FET (ISFET), with a floating gate 318 having a sensor plate 320 optionally separated from the well interior by a passivation layer 316. The sensor 314 can be responsive to (and generate an output signal related to) the amount of a charge 324 present on passivation layer 316 opposite the sensor plate 320. Changes in the charge 24 can cause changes in a current between a source 321 and a drain 322 of the chemFET. In turn, the chemFET can be used directly to provide a current-based output signal or indirectly with additional circuitry to provide a voltage-based output signal. Reactants, wash solutions, and other reagents may move in and out of the wells by a diffusion mechanism 340.

In an embodiment, reactions carried out in the well 301 can be analytical reactions to identify or determine characteristics or properties of an analyte of interest. Such reactions can generate directly or indirectly byproducts that affect the amount of charge adjacent to the sensor plate 320. If such byproducts are produced in small amounts or rapidly decay or react with other constituents, then multiple copies of the same analyte may be analyzed in the well 301 at the same time in order to increase the output signal generated. In an embodiment, multiple copies of an analyte may be attached to a solid phase support 312, either before or after deposition into the well 301. The solid phase support 312 may be microparticles, nanoparticles, beads, solid or porous comprising gels, or the like. For simplicity and ease of explanation, solid phase support 312 is also referred herein as a particle or bead. For a nucleic acid analyte, multiple, connected copies may be made by rolling circle amplification (RCA), exponential RCA, or like techniques, to produce an amplicon without the need of a solid support.

In particular, reactions resulting in the extension of an oligonucleotide, such as a primer, or reactions otherwise forming copies of a target DNA or RNA utilize reagent solutions that include nucleic acids. In an example, the reagent solution is an aqueous solution including a biomer, tris(2-carboxyethyl)phosphine (TCEP), and water. The reagent solution can further include a surfactant, salt, a biocidal agent, or a combination thereof.

For example, the reagent solution can include TCEP in a range of 0.5 μM to 1000 μM. In an example, the TCEP can be included in the reagent solution in an amount in a range of 0.5 μM to 100 μM, such as a range of 0.5 μM to 10 μM, a range of 0.5 μM to 5 μM, or a range of 0.5 μM to 1 μM.

A biomer is a unit useful in forming biopolymers, such as nucleic acids, ribonucleic acids or proteins. For example, a biomer can be a nucleotide, a ribonucleotide, an amino acid, or a combination thereof. An example nucleotide can be selected from thymine, cytosine, adenine, guanine, uracil or a combination thereof. Alternatively, the nucleotide can be selected from thymine, cytosine, adenine, guanine, or a combination thereof. Example ribonucleotides can have similar bases to the above identified nucleotides.

The biomer can be present in the reagent solution in a range of 100 nM or 200 μM. For example, the biomer can be present in the reagent solution in a range of 1 μM to 100 μM, such as a range of 10 μM to 100 μM. In an example, a nucleotide can be present in the reagent solution in a range of 100 nM or 200 μM. For example, the nucleotide can be present in the reagent solution in a range of 1 μM to 100 μM, such as a range of 10 μM to 100 μM.

In addition, the reagent solution can further include a surfactant. For example, the surfactant can be present in a range of 0.001% to 10%, such as a range of 0.001% to 1%, or a range of 0.001% to 0.1%.

The surfactant can be an ionic surfactant, an amphoteric surfactant, or a non-ionic surfactant. The ionic surfactant can be an anionic surfactant. In another example, the ionic surfactant can be a cationic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate; or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

An exemplary cationic surfactant includes primary, secondary or tertiary amines, quaternary ammonium surfactants, or any combination thereof. An exemplary quaternary ammonium surfactant includes alkyltrimethylammonium salts such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl)dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin.

In a further example, the surfactant can be a non-ionic surfactant, such as a polyethylene glycol-based surfactant, for example, including a polyethylene glycol moiety. In an example, the polyethylene glycol-based surfactant includes a phenyl ether of polyethylene glycol. In another example, the surfactant can be a non-ionic surfactant, such as a block copolymer including poly(ethylene oxide) or a tri-block copolymer including poly(ethylene oxide). For example, the surfactant can include a poly(ethylene oxide)/poly(propylene oxide) block copolymer.

The reagent solution can further include salts, such as sodium chloride, magnesium sulfate, or a combination thereof. In an example, sodium chloride can be included in the reagent solution in an amount of 0.01 M to 2 M. For example, the sodium chloride can be included in the reagent solution in an amount of 0.01 M to 1 M, or an amount of 0.01 M to 0.5 M.

The solution can include magnesium sulfate, which, for example, can be included in the reagent solution in an amount of 0.001 M to 2 M. For example, the magnesium sulfate can be included in the reagent solution in an amount of 0.001 M to 1 M, such as an amount of 0.001 M to 0.1 M.

Optionally, the reagent solution can include a biocidal agent, such as an antimicrobial agent. An example biocidal agent includes an isothiazolinone compound or derivatives thereof. For example, the isothaizolinone compound can include isothiazolinone, methylisothiazolinone, chloromethylisothiazolinone, benzisothiazolinone, octylisothiazolinone, dichlorooctylisothiazolinone, butylbenzisothiazolinone, or a combination thereof. The biocidal agent, such as an isothiazolinone compound, can be included in the reagent solution in an amount of 0.001% to 1%, such as an amount of 0.001% to 0.1%.

In another example, a wash solution includes water, a non-ionic surfactant, a biocidal agent and tris(2-carboxyethyl)phosphine. Such a wash solution can be applied to flush a reagent solution or during parts of a process in which biomers are not required. In another example, the wash solution can be used to form a reagent solution.

For example, the wash solution can include TCEP in a range of 0.5 μM to 1000 μM. In an example, the TCEP can be included in the wash solution in an amount in a range of 0.5 μM to 100 μM, such as a range of 0.5 μM to 10 μM, a range of 0.5 μM to 5 μM, or a range of 0.5 μM to 1 μM.

In addition, the reagent solution can further include a surfactant. For example, the surfactant can be present in a range of 0.001% to 10%, such as a range of 0.001% to 1%, or a range of 0.001% to 0.1%.

The surfactant can be an ionic surfactant, an amphoteric surfactant, a non-ionic surfactant, or a combination thereof. The surfactant can be selected from the above surfactants. In an example, the surfactant is a non-ionic surfactant. For example, the surfactant can be a non-ionic surfactant, such as a polyethylene glycol-based surfactant, for example, including a polyethylene glycol moiety. In an example, the polyethylene glycol-based surfactant includes a phenyl ether of polyethylene glycol. In another example, the surfactant can be a non-ionic surfactant, such as a block copolymer including poly(ethylene oxide) or a tri-block copolymer including poly(ethylene oxide). For example, the surfactant can include a poly(ethylene oxide)/poly(propylene oxide) block copolymer.

The wash solution can further include salts, such as sodium chloride, magnesium sulfate, or a combination thereof. In an example, sodium chloride can be included in the reagent solution in an amount of 0.01 M to 2 M. For example, the sodium chloride can be included in the reagent solution in an amount of 0.01 M to 1 M, or an amount of 0.01 M to 0.5 M.

The wash solution can include magnesium sulfate, which, for example, can be included in the wash solution in an amount of 0.001 M to 2 M. For example, the magnesium sulfate can be included in the wash solution in an amount of 0.001 M to 1 M, such as an amount of 0.001 M to 0.1 M.

Optionally, the wash solution can include a biocidal agent, such as an antimicrobial agent. An example biocidal agent includes an isothiazolinone compound or derivatives thereof. For example, the isothaizolinone compound can include isothiazolinone, methylisothiazolinone, chloromethylisothiazolinone, benzisothiazolinone, octylisothiazolinone, dichlorooctylisothiazolinone, butylbenzisothiazolinone, or a combination thereof. The biocidal agent, such as an isothiazolinone compound, can be included in the wash solution in an amount of 0.001% to 1%, such as an amount of 0.001% to 0.1%.

Optionally, the wash solution can include a solid buffer particulate. The solid buffer particulate can include a ceramic particulate. In an example, the ceramic particulate can be titanium dioxide, tin oxide, zirconia, alumina, tantalum oxide, or a combination thereof. For example, the ceramic particulate can be a titanium dioxide or tin oxide. In a particular example, the ceramic particulate includes titanium dioxide (i.e., titania). Further, the ceramic particulate can be a hydrolyzed ceramic particulate or can be a fumed ceramic particulate. In particular, the ceramic particulate is a fumed ceramic particulate.

The solid buffer particulate, such as a ceramic particulate, can have a point of zero charge at least 1.2 pH units different than the target pH. For example, the point of zero charge can be at least 2.0 pH units different than a target pH or at least 3.0 pH units different than the target pH, but not greater than 10 pH units different than the target pH. In particular, the solid buffer particulate has a point of zero charge that is less than the target pH of the suspension. Alternatively, the solid buffer particulate can have a point of zero charge that is greater than the target pH of the suspension. In a further alternative, a combination of solid buffer particulates can be used. For example, a combination including a solid buffer particulate having a point of zero charge below the target pH and a solid buffer particulate having a point of zero charge above the target pH can be used.

Further, the solid buffer particulate can have a specific surface area in the range of 10 $m^2/g$ to 350 $m^2/g$. For example, the specific surface area can be in a range of 50 $m^2/g$ to 350 $m^2/g$, such as a range of 100 $m^2/g$ to 300 $m^2/g$, a range of 150 $m^2/g$ to 300 $m^2/g$, or even a range of 225 $m^2/g$ to 275 $m^2/g$. In another example, the specific surface area can be in a range of 25 $m^2/g$ to 125 $m^2/g$, such as a range of 50 $m^2/g$ to 100 $m^2/g$. Further, the solid buffer particulate can have a particle size, such as an average agglomerate size, in a range of 0.01 μM to 1200 μM. For example, the average particle size can be in a range of 0.05 μM to 500 μM, such as a range of 0.5 μM to 200 μM, or even a range of 5.0 μM to 100 μM.

The wash solution can include the solid buffer particulate (e.g., titania) in a range of 0.0001 g/mL to 0.01 g/mL, such as a range of 0.0005 g/mL to 0.01 g/mL, a range of 0.0010 g/mL to 0.0065 g/mL, a range of 0.0010 g/mL to 0.0050 g/mL, or even a range of 0.0010 g/mL to 0.0040 g/mL.

The wash solution can be used to form a reagent solution including a biomer, such as those listed above. For example, the biomer can be in the wash solution in amounts in the ranges listed above. In particular, the reagent solution formed from the wash solution can include a nucleotide.

EXAMPLE

Example 1

Reagent solutions are prepared with and without TCEP. The solutions are tested using an ION S5 XL modified with larger reagent containers.

The reagent solutions include 0.1 M sodium chloride, 0.015 M magnesium chloride, 0.01% Pluronic® F68, and 0.05% Neolone™. The reagent solution including TCEP, includes TCEP in an amount of 2%.

Figure 4:
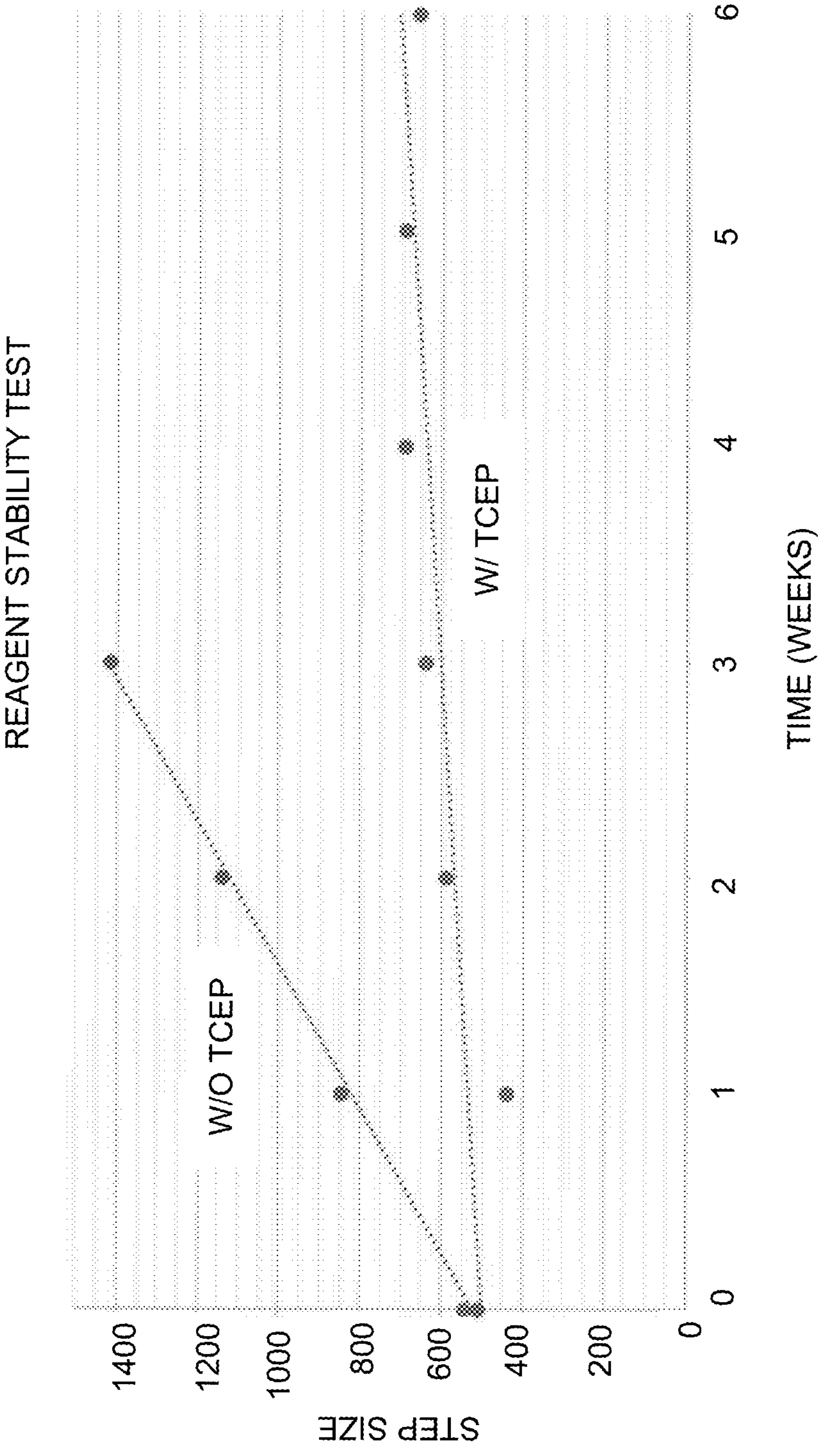
FIG. 4 include a graph illustrating stability of reagent solutions.

The pH was tested relative to a buffered test solution using a 540 chip on an ION S5 XL sequencer. The average step response switching from the buffered solution to the reagent solution is determined. The process is repeated weekly for 6 weeks with the reagent solutions aging at room temperature between tests. As illustrated in FIG. 4, the reagent solution without TCEP shows a significant step change with each passing week, whereas the reagent solution with TCEP shows little change in pH over a 6-week period.

Example 2

A reagent solution with TCEP is further tested for effectiveness when used for a sequencing run. Sequencing performance is tested with a standard 200 bp library kit (Ampliseq® Exome 200 bp Control Library) for sample preparation using the ION Chef (ION Chef v2 kit) and an ION 540 chip. Sequencing is performed after aging each week for 6 weeks using an Ion Torrent S5.

A reagent solution having the composition 106 nM NaCl, 17 mM MgSO4, 0.05 wt. % isothiazolinone, 0.01% Triton X-100, 0.0013 g/ml titania, and 2 μM TCEP is used to prepare nucleotide solutions for each of thymine, cytosine, adenine, and guanine. The titania is filtered from the solution before mixing with the nucleotide.

As illustrated in Table 1, sequencing performance remains substantially consistent over the 6-week period.

TABLE 1

Sequencing Performance for Aging Reagent Solution

| | Week 0 | Week 1 | Week 2 | Week 3 | Week 4 | Week 5 | Week 6 |
|---|---|---|---|---|---|---|---|
| Total Number of Reads | 81.2M | 83.9M | 77.6M | 72.5M | 76.2M | 81.0M | 68.2M |
| Total Bases AQ20 (Mbp) | 11.0k | 12.5k | 11.1k | 10.1k | 10.5k | 11.1k | 9.21k |
| Mean Length AQ20 (bp) | 158 | 167 | 162 | 159 | 159 | 157 | 156 |
| Average Raw Read Accuracy | 98.86% | 98.98% | 98.87% | 98.82% | 98.80% | 98.80% | 98.93% |
| Key Signal (Value) | 79 | 85 | 83 | 85 | 81 | 88 | 85 |

The above reagent and wash solutions exhibit particular technical advantages, including extended shelf life. It is believed that the components interact to advantageously prevent degradation of other components.

In a first aspect, a reagent solution includes water, a nucleotide, and tris(2-carboxyethyl)phosphine in a range of 0.5 μM to 1000 μM.

In an example of the first aspect, the range is 0.5 μM to 100 μM. For example, the range is 0.5 μM to 10 μM.

In another example of the first aspect and the above examples, the nucleotide is selected from thymine, cytosine, adenine, or guanine.

In a further example of the first aspect and the above examples, the nucleotide is present in a range of 100 nanomolar to 500 μM. For example, the nucleotide is present in a range of 1 μM to 200 μM.

In an additional example of the first aspect and the above examples, the reagent solution further includes a surfactant. For example, the surfactant is present in a range of 0.001% to 10%, such as a range of 0.001% to 1% or a range of 0.001% to 0.1%. In an example, the surfactant is a non-ionic surfactant. For example, the non-ionic surfactant includes a triblock copolymer. In an example, the surfactant includes a poly (ethylene oxide) moiety. In a further example, the non-ionic surfactant includes a polyethylene oxide copolymer, such as a poly(ethylene oxide)/poly(propylene oxide) block copolymer.

In another example of the first aspect and the above examples, the reagent solution further includes sodium chloride. For example, the sodium chloride is included in an amount of 0.01 M to 2 M. In an example, the sodium chloride is included in an amount of 0.01 M to 1 M, such as in an amount of 0.01 M to 0.5 M.

In a further example of the first aspect and the above examples, the reagent solution further includes magnesium sulfate. For example, the magnesium sulfate is included in an amount of 0.001 M to 2 M. In an example, the magnesium sulfate is included in an amount of 0.001 M to 1 M, such as in an amount of 0.001 M to 0.1 M.

In an additional example of the first aspect and the above examples, the reagent solution further includes a biocidal agent. For example, the biocidal agent is included in an amount of 0.001% to 1%. In an example, the biocidal agent is included in an amount of 0.001% to 0.1%. In a further example, the biocidal agent is an isothiazolinone compound.

In a second aspect a reagent solution includes water, a non-ionic surfactant in an amount of 0.001% to 1%, biocidal agent in an amount 0.001% to 1%, and tris(2-carboxyethyl) phosphine in a range of 0.5 μM to 1000 μM.

In an example of the second aspect, the tris(2-carboxyethyl)phosphine is included in a range of 0.5 μM to 100 μM. For example, the tris(2-carboxyethyl)phosphine is included in a range is 0.5 μM to 10 μM.

In another example of the second aspect and the above examples, the reagent solution further includes a biomer. For example, the biomer includes a nucleotide. In an example, the nucleotide is selected from thymine, cytosine, adenine, or guanine. In a further example, the biomer is included in an amount of 100 nanomolar to 500 μM. For example, the biomer is present in a range of 1 μM to 200 μM.

In a further example of the second aspect and the above examples, the non-ionic surfactant is present in a range of 0.001% to 0.1%. In an example, the non-ionic surfactant includes a triblock copolymer. In a further example, the triblock copolymer includes a poly (ethylene oxide) copolymer, such as a poly(ethylene oxide)/poly(propylene oxide) block copolymer. In an additional example, the non-ionic surfactant includes a poly (ethylene oxide) moiety.

In an additional example of the second aspect and the above examples, the reagent solution further includes sodium chloride. For example, the sodium chloride is included in an amount of 0.01 M to 2 M. In an example, the sodium chloride is included in an amount of 0.01 M to 1 M, such as in an amount of 0.01 M to 0.5 M.

In another example of the second aspect and the above examples, the reagent solution further includes magnesium sulfate. For example, 44. the magnesium sulfate is included in an amount of 0.001 M to 2 M. In an example, the magnesium sulfate is included in an amount of 0.001 M to 1 M, such as in an amount of 0.001 M to 0.1 M.

In a further example of the second aspect and the above examples, the biocidal agent is included in an amount of 0.001% to 0.1%.

In an additional example of the second aspect and the above examples, 48 the biocidal agent is an isothiazolinone compound.

In another example of the second aspect and the above examples, the reagent solution further includes titania particulate. For example, the titania particulate is included in an amount of 0.0005 g/ml to 0.01 g/ml.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A reagent solution comprising:

water;

a non-ionic surfactant in an amount of 0.001% to 1%;

biocidal agent in an amount of 0.001% to 1%;

tris(2-carboxyethyl) phosphine in a range of 0.5 μM to 1000 μM; and titania particulate.

2. The reagent solution of claim 1, wherein the tris(2-carboxyethyl) phosphine is included in a range of 0.5 μM to 100 μM.

3. The reagent solution of claim 2, wherein the tris(2-carboxyethyl) phosphine is included in a range is 0.5 μM to 10 μM.

4. The reagent solution of claim 1, further comprising a biomer.

5. The reagent solution of claim 4, wherein the biomer includes a nucleotide.

6. The reagent solution of claim 5, wherein the nucleotide is selected from thymine, cytosine, adenine, or guanine.

7. The reagent solution of claim 4, comprising the biomer in an amount of 100 nanomolar to 500 μM.

8. The reagent solution of claim 7, wherein the biomer is present in a range of 1 μM to 200 μM.

9. The reagent solution of claim 1, wherein the non-ionic surfactant is present in a range of 0.001% to 0.1%.

10. The reagent solution of claim 1, wherein the non-ionic surfactant includes a triblock copolymer.

11. The reagent solution of claim 10, wherein the triblock copolymer is a poly(ethylene oxide)/poly(propylene oxide) block copolymer.

12. The reagent solution of claim 1, wherein the non-ionic surfactant includes a poly (ethylene oxide) moiety.

13. The reagent solution of claim 1, further comprising sodium chloride.

14. The reagent solution of claim 13, wherein the sodium chloride is included in an amount of 0.01 M to 2 M.

15. The reagent solution of claim 14, wherein the sodium chloride is included in an amount of 0.01 M to 1 M.

16. The reagent solution of claim 1, further comprising magnesium sulfate.

17. The reagent solution of claim 16, wherein the magnesium sulfate is included in an amount of 0.001 M to 2 M.

18. The reagent solution of claim 1, wherein the biocidal agent is included in an amount of 0.001% to 0.1%.

19. The reagent solution of claim 1, wherein the biocidal agent is an isothiazolinone compound.

* * * * *